(12) United States Patent
Keenan et al.

(10) Patent No.: US 8,679,051 B2
(45) Date of Patent: Mar. 25, 2014

(54) MICROBUBBLE MEDICAL DEVICES (75) Inventors: James A Keenan, Ottawa (CA); Junjie Gu, Ottawa (CA); Philippe Joel Genereux, Ottawa (CA); Adrian T Bienkinsop, Ottawa (CA); David H Gerwing, Ottawa (CA); Sebastien Roy Fournier, Lachute (CA); Sarah Katherine Dobbin, Ottawa (CA)

(73) Assignee: Artenga Inc, Ottawa (CA)

( * ) Notice: Subject to any disclaimer, the term of this patent is extended or adjusted under 35 U.S.C. 154(b) by 447 days.

(21) Appl. No.: 12/683,601

(22) Filed: Jan. 7, 2010

(65) Prior Publication Data

US 2010/0228122 A1 Sep. 9, 2010

Related U.S. Application Data (63) Continuation of application No. 11/588,995, filed on Oct. 27, 2006, now abandoned.

(60) Provisional application No. 60/730,370, filed on Oct. 27, 2005.

(51) Int. Cl.
*A61M 37/00* (2006.01)

(52) U.S. Cl.
USPC ............. 604/24; 604/500; 600/437; 424/9.52

(58) Field of Classification Search
USPC ............... 604/23, 24, 26, 500, 506, 507, 508, 604/518, 519; 600/437, 439, 458; 424/9.52
See application file for complete search history.

(56) References Cited

U.S. PATENT DOCUMENTS

| | | | |
|---|---|---|---|
| 5,425,580 A * | 6/1995 | Beller | 366/131 |
| 6,306,094 B1 | 10/2001 | Joseph | |
| 6,890,332 B2 | 5/2005 | Truckai et al. | |
| 2002/0026117 A1 | 2/2002 | Joseph | |
| 2003/0125727 A1 | 7/2003 | Truckai et al. | |
| 2003/0191396 A1* | 10/2003 | Sanghvi et al. | 600/476 |
| 2004/0253183 A1 | 12/2004 | Uber | |

FOREIGN PATENT DOCUMENTS

| | | |
|---|---|---|
| WO | WO98/18387 A1 | 5/1998 |
| WO | WO02/47744 A2 | 6/2002 |
| WO | WO2005/105181 A1 | 11/2005 |

* cited by examiner

*Primary Examiner* — Kami A Bosworth
(74) *Attorney, Agent, or Firm* — Albert Peter Durigon (57) ABSTRACT

Method and medical devices for generating and stabilizing micro- or nano-bubbles, and systems and methods for therapeutic applications using the bubbles, are provided. The micro-bubbles may be used to enhance therapeutic benefits such as ultrasound-guided precision drug delivery and real-time verification, acoustic activation of large tumor masses, enhanced acoustic activation through longer retention of therapeutic agents at the point of interest, enhancement of high intensity focused ultrasound treatments, light activation of photodynamic drugs at a depth within a patient using extracorporeal light sources, probes, or sonoluminescence, and initiation of time reversal acoustics focused ultrasound to permit highly localized treatment.

16 Claims, 8 Drawing Sheets

MICROBUBBLE MEDICAL DEVICES

CROSS-REFERENCE TO RELATED APPLICATIONS

This application is a continuation of application Ser. No. 11/588,995, filed on Oct. 27, 2006, the entire disclosure of which is hereby incorporated by reference for all purposes.

This non-provisional application claims the benefit of U.S. Provisional Application No. 60/730,370 filed Oct. 27, 2005, which is hereby incorporated by reference.

FIELD OF THE INVENTION

The invention generally pertains to medical devices for infusing therapeutic agents into patients and more particularly to medical devices for generating gas bubbles suitable for infusion into patients. Such devices can be used, for example, to inject or otherwise administer therapeutic agents in the form of, or in combination with, micro or nano bubbles. Acoustic activation or sonoporation of the bubbles, through the application of ultrasound energy, increases cell permeability and improves drug uptake and treatment efficacy. Variants of the method, system, and device may incorporate fluid flow focusing, cross flow bubble detachment, bubble stability through rectified diffusion, surfactant combinations, bioadhesion additives, sonophoresis, photodynamic drugs, tumour killing agents, contrast agents, time reversal acoustics focused ultrasound, high intensity focused ultrasound, and sonoluminescence. Variants of the method, system, and device may be used to produce contrast media to enhance ultrasound imaging.

BACKGROUND TO THE INVENTION

Acoustic activation is a means to improve the effectiveness of drugs.

A variety of acoustically activated drug delivery systems exist including gas bubbles and drugs, drugs encapsulated in microspheres, biodegradable polymer and drug solution gas bubbles, drug impregnated microsponges, injectable nanoparticles such as vesicles, micelles, and liposomes, and other drug carrying particles, bubbles, or spheres that permit acoustic activation of therapeutic agents.

Acoustically activated drug delivery systems are typically administered to a patient and then activated by extracorporeal ultrasound sources to increase the permeability of cell membranes to allow drugs to better penetrate cells, enhance drug uptake, and hence improve the treatment efficacy.

Acoustic activation may permit localized drug delivery. The physician may apply ultrasound once the drug and cavitation nuclei, typically microbubbbles, are delivered to a point of interest within a patient, in order to release the drug at the disease site. Localized drug delivery permits a high dosage of toxic drugs to improve treatment effectivness and may minimize negative side effects to healthy tissue.

Ultrasound energy may cause gas microbubbles to resonate or burst into smaller fragments, and may induce cavitation, microstreaming, or the perforation of cell membranes. Bubble resonance is typically described as sonoporation or non-inertial cavitation, while the bubble destruction is described as inertial cavitation.

The therapeutic agents may be chemotherapy drugs, gene therapy, and other agents.

Direct injection of chemotherapy drugs into tumours is typically not done, as this does not improve patient outcome. Cancers may develop resistance to drugs and render chemotherapy useless. Acoustic activation researchers have destroyed human, drug-resistant tumours in rodents using cavitation nuclei and ultrasound.

Acoustic activation technology shows promise for the treatment of drug resistant cancer tumours, vascular disease, neurological diseases, and other diseases. Efficacy may be enhanced by infusing drugs with bubbles and enhancing cell permeability with ultrasound energy. Further benefits may be obtained by infusing transient gas microbubbles in combination with acoustically activated drug delivery release systems to enhance the local cavitation effects.

Presently, acoustically activated drug delivery systems are typically hard-shelled, persistent, gas microbubbles formulated in a pharmaceutical setting. They are designed to persist through to administration to a patient. Such products are required to maintain integrity through the shock, vibration, and temperature changes of transportation and to persist over time through to administration. Such formulations may include complex design and processing features, for example, are typically polymer or polymer and solvent based. However, these persistent systems must also dissipate or degrade in the patient once administered and activated. These polymers and any other components are required to biodegrade with minimal negative side effects.

Acoustically activated drug delivery systems may range in size from nano scale, sub micron, up to 1000 microns, with a one to ten micron size typical. Size preference depends upon the resonant frequency, or a harmonic, of the bubble or particle to be activated at a particular ultrasound frequency, and may also depend upon the desired release rates of the encapsulated drugs. Increased size uniformity would encourage effective and more complete activation.

Acoustic activation techniques include inertial cavitation, where typically 20 micron gas microbubbles are destroyed by ultrasound energy, and non-inertial cavitation or sonoporation, where ultrasound energy causes one to seven micron microbubbles to resonate. Researchers have demonstrated in vivo therapeutic enhancement with both techniques. In addition, sonophoresis involves the application of ultrasound, or ultrasound and cavitation nuclei such as microbubbles, to increase the permeability of surface cells, such as the skin or cornea, in order to improve the delivery of topically applied drugs.

In the field of oncology, treatment techniques may include administration to patients of individual 'cocktails' of chemotherapy drugs depending upon the indication, patient reaction to therapy, and disease stage. Future treatment planning may include the administration of a first chemotherapy drug enhanced by inertial cavitation followed by a second drug enhanced by non-inertial cavitation.

Oncologists do not currently have a means to provide patients with a flexible, acoustically activated therapy, i.e. the means to administer a variety of drugs, or combination of drugs, on short notice, with therapeutic enhancements such as improved drug uptake and reduced side effects.

Photodynamic drugs are light activated by laser or other sources in order to improve their effectiveness. They are limited to surface applications of about one centimeter in depth or, through the use of a balloon catheter equipped with a laser, may be used to treat internal surfaces of the body for diseases such as cancer of the esophagus. The means to improve the cellular uptake of photodynamic drugs using acoustic activation may improve their effectiveness. The means to light activate photodynamic drugs at a depth within a patient would expand their potential usage.

High intensity focused ultrasound (HIFU) is a means to induce cell necrosis in diseased tissue, for example to destroy tumours through heat ablation. Heat ablation treatments typically require a duration of minutes, which may preclude multiple direct probe applications if patients are in overall poor health and require a number of tumours to be destroyed. The simultaneous infusion of gas microbubbles with HIFU energy may enhance the treatment efficacy and expand potential applications.

Accordingly, there is a need for a medical device that would overcome these and other drawbacks.

SUMMARY OF THE INVENTION

A method and medical device for generating transient micro or nano bubbles, and a system and methods for acoustical activation of the bubbles, is disclosed. Two novel bubble generating means are disclosed: in-line capillary tubes and mix chambers flow focusing, and cross flow bubble generation with optimized bubble detachment means. A method and medical device to stabilize bubble sizes and achieve high homogeneity through rectified diffusion is disclosed. Methods, systems, and devices to permit precision direct drug delivery are disclosed. Methods, systems, selected additives, and devices to permit therapeutic applications such as acoustic activation of large tumour masses while avoiding acoustic shadowing, enhanced acoustic activation through longer retention of therapeutic agents at the point of interest, on demand means for combining inertial and non-inertial acoustic activation in a single treatment, enhancement of high intensity focused ultrasound tumour ablation, activation of photodynamic drugs at a depth within a patient using sonoluminescence and other means, and initiation of time reversal acoustics focused ultrasound to permit highly localized treatment, are disclosed.

The medical device comprises a fluid vessel for holding a fluid, a fluid delivery means operatively connected to the fluid vessel for applying a pressure and causing the fluid to travel a flow path, and a bubble generating means for generating bubbles comprised of the fluid. The fluid passing through the bubble generating means, also termed herein as "bubble fluid". The bubbles generated are micro or nano sized.

The bubble fluid may form bubbles within a second carrier fluid. The second carrier fluid may be contained within a second vessel or within a conduit into which both the bubble fluid and the second fluid flows. Additional fluids are also contemplated. An injection means for delivering the bubble fluid co-mingled with the second fluid into a body at a desired location, for example, into a tissue mass, tumour, muscle, skin, organ, or other suitable structure, depending on the application, may also be provided.

Ultrasound may then be used to rupture, resonate, or otherwise activate the bubbles (acoustic activation) at a point of interest.

The injection means include a hollow needle, catheter, tube, or other surgical instrument that can be inserted within a body to a point of interest, for example, into a tissue mass, tumour, muscle, skin, organ, vein, artery, or other suitable structure, depending on the application, and is structured to permit fluid flow. Fluid from the vessel would be able to flow through the injection means for discharge into the body, or more specifically, at a point of interest. The term "injection means" is to be broadly understood as including various means for introducing a fluid into a body, including by active injection or passive permeation, or otherwise by infusion.

The device may be used to infuse microbubbles in order to enhance the heat ablation effects of therapeutic ultrasound. Such therapeutic ultrasound may be applied non-invasively through an extracorporeal transducer or transducer array or through minimally invasive means, such as a high intensity focused ultrasound (HIFU) probe. The hollow needle, catheter, or tube to be used for microbubble infusion may be connected to a HIFU probe, or mounted coaxially or through other suitable means for focusing ultrasound and microbubbles at a point of interest. The microbubble infusion means, for example a needle or catheter, may be deployed in conjunction with a HIFU probe, manipulated by a single physician or by two physicians or medical technicians. The heat ablation enhancement of therapeutic ultrasound may or may not be used in combination with drugs, including acoustically activated drugs.

All or part of the device may be mounted on a handheld device or connected by conduit to the handheld device, such as a compressed, medical grade gas canister connected by conduit to the device. The means for generating bubbles may be a separate assembly from the handheld device. The device and means for generating bubbles may be configured as a table top or floor-supported unit, locally mounted, supported on patient body parts, or configured in other means suitable to a clinical setting. The device may be connected to building utilities, for example to a hospital oxygen gas supply line.

The fluid may be a liquid or gas, including in the form of a solution, a suspension, a vapour, other fine particulate solids dissolved in a liquid vehicle, a combination, or the like, provided that it is flowable. This fluid may be added to a second fluid which may also be in the form of a solution, a suspension, a vapour, other fine particulate solids dissolved in a liquid vehicle, a combination, or the like, provided that it is flowable. Thus, the device may be used to generate gas bubbles within a liquid carrier, liquid bubbles/droplets within a liquid carrier, liquid bubbles/droplets within a gas carrier, or gas bubbles within a gas carrier. The device may be used with liquefied gas.

The fluid vessel is any vessel that can hold and dispense fluid. For example, the vessel may be in the form of a syringe and the fluid delivery means may be in the form of a plunger for the syringe or a pump. As another example, the fluid vessel may be in the form of a compressed gas vessel and the fluid delivery means in the form of a compressed gas force and suitable regulators. The term "container" may be understood as interchangeable with the term "vessel".

The fluid vessel may contain a therapeutic fluid or a carrier fluid. A therapeutic fluid may be a therapeutic liquid, such as a liquid drug or drug in solution, or contain a therapeutic agent suspended, dissolved, carried, or otherwise conveyed in a suitable liquid vehicle including drug eluting microspheres suspended in a fluid and radiolabelled isotopes. A therapeutic agent may include a variety of drug compounds, or other medicinal or non-medicinal substances, minerals, vitamins, imaging-enhancement substances, radioactive substances, and the like, that can be carried in the liquid or gaseous fluid.

The carrier or bubble fluids may include additives, natural or synthetic, to alter its viscosity, or a surfactant or a combination of surfactants, in order to promote the generation of or the stability of bubbles, and effective drug perfusion.

The additives may be toxic, for example surfactants with a beta-lactam ring that may destroy cells by necrosis. An advantage of such a component is to efficiently perform combination therapy. A single additive may improve bubble stability and generation, in order to promote acoustic activation of a chemotherapy drug, as well as enhance tumour cell destruction through necrosis.

The carrier or bubble fluids may include additives, for example fibrin compounds, to promote the bioadhesion of the bubbles or therapeutic agents. The advantage of bioadhesion additives would be to promote the retention of the bubbles or the therapeutic agent within a diseased site, for example a tumour, despite the tendency of a tumour's vascular network to drain fluids away. In this way the acoustic activation may be prolonged to ensure sufficient duration, such as a minute or a few minutes of ultrasound application, for optimum therapeutic effects.

Additives that increase the viscosity of the drug, without particular bioadhesive properties, may also improve the retention of the bubbles or the therapeutic agent by slowing their drainage from a tumour. For example, PVP povidone is a common medical thickening agent.

The carrier or bubble fluids may include additives that are disposed to improve therapeutic agent uptake in cancer cells. For example, lipidiol bound to a radioisotope is administered via catheter for the treatment of liver cancers.

The carrier or bubble fluids may include additives chemically compatible with specific therapeutic agents, for example an alcohol-compatible surfactant. This may permit acoustic activation of treatments such as direct ethanol or acid injection in tumours, or injection of liquid radioisotopes or radioactive particles in suspensions.

Ethanol injection of liver tumours is an established, inexpensive treatment, however it is limited to tumour sizes of around 2 cm or less, even distribution throughout the tumour mass may be problematic, and five year survival of only 60% is typical. As alcohol destabilizes some surfactants, an alcohol compatible surfactant would be selected so that the device may be used to acoustically activate and improve ethanol injection effectiveness and to permit its use for larger tumours.

The device may include means for intermixing additives on demand with the fluids in order to provide patient specific treatment. For example, gas bubbles without bioadhesion or viscosity enhancing additives could be administered in a sterile saline solution to enhance ultrasound imaging clarity of a local anatomical region, such as a tumour. The device could then be used to infuse a chemotherapy drug with gas bubbles and bioadhesion and viscosity enhancing additives in order to optimize the bubble stability and retention in the tumour site for the application of ultrasound and acoustic activation of the drug.

The device may include an ultrasonic transducer or transducer array in order to stabilize bubbles at desired sizes using rectified diffusion. Gas bubbles tend to shrink and dissipate in liquids. Rectified diffusion is the process whereby ultrasound energy causes bubbles at a particular size to resonate and prevents further bubble shrinkage for as long as the ultrasound is applied.

An advantage of using rectified diffusion to stabilize bubble size is to permit a simpler, less costly means to generate the desired bubbles. Acoustic activation is typically achieved with gas bubbles from one to twenty microns in diameter, and in particular, one to five microns diameter, and a homogenous size distribution is desired. The device may incorporate relatively simple and inexpensive means for generating non-stable bubbles in a range of sizes, such as twenty to three hundred microns in diameter. As the bubbles shrink to the resonant frequency size of the rectified diffusion ultrasound source, they may be stabilized, resulting in homogenous, small diameter bubbles, which can then be infused into the patient for acoustic activation therapy or imaging purposes.

The device may include means for driving the bubble fluid into a second carrier fluid while inducing cross flow motion in the carrier fluid. This cross flow will promote bubble detachment, permitting smaller and more homogenous bubble sizes than would be possible with a static system. By controlling the cross flow speed, a controllable bubble size can be achieved.

Cross flow experiments whereby the bubble fluid is driven from a capillary tube or pipette into a flowing carrier fluid, and where the capillary tube is mounted at right angles to the flowing carrier fluid, reveal a tendency for the forming bubbles to be driven in the direction of the flow and to expand prior to detachment. As smaller bubbles are typically desired, it is advantageous to have additional means for promoting bubble detachment. The cross flow device may include funnels or hydrofoils to focus the carrier fluid flow at the capillary tube opening for optimum bubble detachment. The capillary tube may be positioned in line of the cross flow. The capillary tube may be subjected to a regular shear force or vibration, through contact with a piezo transducer or other electromechanical means, in order to promote bubble detachment.

The fluid vessel or vessels, conduits, and device may include means for controlling the fluid temperature, such as refrigeration or heating sources, temperature sensors and controls, thermal insulating materials, and the like, to enhance the bubble generation. Temperature control means in combination with fluid pressure control, may enable a suitable fluid in liquid form to be transformed into micro bubbles and infused into the patient, after which body temperature and pressure may cause the bubbles to change to a gas form for acoustic activation. Bubbles generated by the device may be heated to body temperature prior to infusion within the patient in order to ensure that the bubble size remains constant from generation to therapeutic use.

The fluid delivery means causes fluid in the vessel to travel a flow path, usually along a conduit or vessel such as a syringe. The fluid delivery means may be a plunger on a standard medical syringe, a syringe pump, variable speed fluid transfer pump, peristaltic pump, or other means to pump fluids, and also contemplates pressurization in combination with regulators, for example, compressed gas with a gas regulator.

The fluid delivery means may be manually actuated, driven by mechanical means such as compression or extension springs, or other mechanical methods, by electro-mechanical means such as an electric motor, solenoid drive, programmable syringe pump, or other electro-mechanical means, or by pneumatic or hydraulic means. Where the fluid is a compressed gas, the fluid delivery means may include compressed gas force and suitable regulators. A variety of means are contemplated and may be selected depending on a variety of factors such as the manner of operation of the bubble generating means, the size of the bubbles, the relative viscosity of the bubble fluid and carrier fluid, and other factors, as will be appreciated. For example, the selection of a non-manual drive means for the bubble and carrier fluids may then be dependent upon sufficient pressure to deliver the fluids through capillary tubes, at a rate of the flow sufficient so as to induce a flow focusing effect whereby the bubbles generated may be of a smaller diameter than the capillary tube diameter.

The therapeutic agent may be delivered to the point of interest prior to, simultaneously with, or after the delivery of the transient bubbles in a carrier fluid. The device may include fluid reservoirs for the therapeutic agent or agents, bubble fluid or fluids, and carrier fluid or fluids.

Devices of the present invention includes means for providing nano or micro bubbles through patient infusion means such as a needle or catheter, to enhance the therapeutic efficacy of a drug.

The device may be comprised of a handheld assembly or of a system, comprised of a handheld assembly connected to other components which may include fluid vessels, pumps, power sources, regulators, meters, and the like.

Using a system, method and medical device of the present invention, transient bubbles may be generated locally at the procedure site, including just prior to or during a drug administration procedure, and acoustically activated without substantial delay. This may result in a less complex therapy system, reduce the need of additives to preserve persistent bubbles generated in pharmaceutical settings, and produce more uniform bubbles. These and other advantages will become apparent to the skilled person.

Using a system, method, and medical device of the present invention, bubble concentration may be varied on demand, including immediately prior to or during a drug administration procedure. If the intent is to infuse a large mass, for example a six to ten centimeter tumour, with chemotherapy drugs and gas bubbles for acoustic activation, minimal bubble concentration to achieve tumour cell destruction could be attained.

Minimal effective bubble concentration may be vital to the success of the treatment in order to avoid acoustic shadowing. Acoustic shadowing would be the absorption of ultrasound energy by the bubbles proximal to the ultrasound transducer, leaving those bubbles distal to the transducer with insufficient ultrasound energy with which to achieve acoustic activation. Acoustic shadowing could cause the proximal tumour cells to be effectively destroyed but the distal tumour cells unaffected. Varying bubble concentration on demand, and verifying the results real time using the ultrasound display, could avoid this problem. These and other advantages will become apparent to the skilled person.

A staged treatment method and medical device of the present invention could be used to avoid acoustic shadowing. For example, the physician could position the needle or catheter at the bottom third of a large tumour, infuse the drug and bubbles and acoustically activate with ultrasound. Once the distal portion of the tumour was treated, the needle or catheter could be repositioned in the central portion of the tumour, and treatment repeated, and then the needle positioned at the proximal portion of the tumour and treatment completed.

Using a system, method, and medical device of the present invention, initiation of a time reversal focused ultrasound array may be permitted.

Time reversal acoustics (TRA) is based on the reversibility of acoustic propagation that the time-reversed version of an incident pressure field naturally refocuses on its source. Researchers have demonstrated the ability of TRA to provide spatial control and focusing of an ultrasonic beam in inhomogeneous media.

A TRA system can produce a more effective spatial concentrating of ultrasound energy than conventional systems, the focus volume can be made close to the ultrasound diffraction limits, and can do so in anatomical regions where conventional ultrasound systems have limited use. For example, despite the severe refractions and scattering of an ultrasonic beam through skull bone, researchers have focused a beam to converge on a 1.5 mm diameter spot.

The TRA and it can be of a complex form or spherical, instead of the long cigar-shaped volumes formed by conventional focusing systems.

The ability to effectively localize ultrasound energy and avoid exposure of surrounding tissues is important in many medical applications.

The main problem that limits application of TRA is the necessity to place an initial pulse source at the chosen point of focusing. The medical device of the present invention permits precise infusion of a drug and bubble cloud within a patient. A conventional ultrasound signal could then be applied and the preferential signal echo from the bubble cloud used as an initial pulse source with which to focus the TRA ultrasound. This would permit a tightly focused TRA signal to acoustically activate a drug within a tumour. Drug and microbubbles that inadvertently dispersed into healthy tissue would not be acoustically activated and hence negative side effects are avoided.

Using a system, method and medical device of the present invention, other means may be used to enhance photodynamic drug effectiveness and to permit use at a depth within a patient.

The device may be used to precisely deliver a photodynamic drug infused with microbubbles to an area of interest. Ultrasound energy application will enhance cellular uptake of the drug and the device disconnected from the needle or catheter. A fiberoptic laser could then be threaded through the needle or catheter in order to apply light energy to photodynamically activate the drug. Alternatively, a needle adapter could be used to permit the extracorporeal application of light energy through the needle to a depth within the patient.

Fiber optic probes have been inserted through thin, 27-gauge needles, in vivo, into tumours in order to sense and quantify tumour fluorescent signals. Such a technique could be used to deliver light at a depth within a patient. Acoustic activation and then subsequent light activation of photodynamic drugs, using conventional light sources, could also be performed as part of an open surgical procedure.

Using a system, method and medical device of the present invention, the phenomena of sonoluminescence may be used to permit photodynamic drug use at a depth within a patient. Sonoluminescence occurs when gas microbubbles collapse due to sound waves and produce light. A diffuse uniformly applied sound wave can focus its energy by over a factor of one trillion to generate a very short flash of ultraviolet light. No clinical medical use for the intriguing phenomenon of sonoluminescence has been established.

In a sonoluminescence application, a method and the device of the present invention may be used to deliver a photodynamic drug at a depth within a patient. The infusion of gas microbubbles and application of ultrasound energy may be used to increase cell permeability and increase drug uptake. The infusion of additional gas microbubbles and high intensity ultrasound may then be used to induce sonoluninescence whereby the collapsing microbubbles light flashes activate the photodynamic drug.

The high intensity ultrasound required to induce sonoluminescence may have undesirable bioeffects. Using a system, method, and medical device that includes a time reversal acoustics focused ultrasound array, the desired ultrasound intensity may be achieved without negative bioeffects.

Using a system, method and medical device of the present invention, therapeutic regimes that require repeat, localized drug injections into a patient may be reduced as the efficacy of an injection is enhanced by acoustic activation. For example, it would be particularly advantageous to reduce the number of repeat needle injections of chemotherapy to the back of the eye to treat retinoblastoma eye cancer.

It is to be appreciated that reference to a "device" of the present invention may be understood to include an "apparatus" or "assembly", which may be incorporated into systems with suitable adaptations.

It is also to be appreciated that the devices of the present invention may be used in a variety of applications, including medical diagnosis, image guided intervention, treatment, surgery, and the like, and also may be used in a similar fashion in veterinary applications and in research applications with suitable modifications.

The term "needle" is intended to include any hollow, slender instrument that may be manipulated to puncture or be inserted or otherwise probe tissues, organs, cavities, or the like. The needle may be used to introduce material into or remove material from a patient or to perform other therapeutic or diagnostic functions. The term needle is intended to include rods or wire-like medical instruments, cannulas, probes, tubes and lumens, stylets, and the like.

The term "patient" may be any suitable animal, including humans and other mammals.

The term "catheter" is intended to include any flexible surgical instrument for the introduction of fluids into the body, including catheters for repeat dose drug delivery such as hickman lines, PORTACATH™ lines and the like.

The fluids container may be any suitable vessel to contain gases or liquids, such as syringes, gas tanks, a central, building-supply, fluid source that may be connected to the device via fluid conduit, and the like.

The fluid delivery means may be a syringe plunger actuated manually, a syringe pump, a variable speed fluid transfer pump, a peristaltic pump, the regulated release of compressed gas, or other suitable means to supply fluids. The delivery means may also be driven manually or by mechanical means such as compression or extension springs, or other mechanical methods, by electro-mechanical means such as an electric motor, solenoid drive, or other electro-mechanical means, or by pneumatic or hydraulic means.

The fluid delivery means may incorporate linked fluid vessels for simultaneous actuation, for example a gear rack, multiple syringe system. A control lever could actuate a mechanical rack, linked to two syringe plungers, with the ratio of plunger actuation varied through the engagement of different gears. Actuating the syringe plunger of a drug-filled syringe would simultaneously actuate the syringe plunger of a microbubble and saline filled syringe with the two fluids intermixing prior to infusion within a body. Through engaging different gears, a physician could adjust the concentration of microbubbles in a drug on demand, and verify the results real time through an ultrasound display.

Linked fluid vessels with simultaneous, multi-fluid intermixing at controlled, variable fluid ratios may be accomplished through a variety of means including manual, mechanical, pneumatic, hydraulic, and electro-mechanical means. A programmable embodiment of the invention with a plurality of micro DC motors, encoders, and electronic circuits, may be used to actuate a plurality of fluid vessels on demand. The gear box assembly or alternative fluid vessel linkage systems may include the operator option of non-linking a fluid vessel, for example the option to deliver a drug without the intermixing of microbubbles.

The means for combining fluids from two containers, for example to intermix a drug with a solution of gas microbubbles in sterile saline, prior to infusion within a patient may include a septum system. Sterile syringes containing different injectates may be loaded into a device. The syringes may have short needles that can be used to puncture a septum, said septum used to seal a sterile needle adaptor or catheter adaptor. The advantage of such a system is to permit a simpler device and loading procedure than would be required to connect syringes with multi-way sterile fluid conduits and valves.

Over all, it is to be appreciated that terms used herein are to be interpreted and understood expansively and not strictly.

The foregoing summarizes the principal features of the invention and some of its optional aspects. The invention may be further understood by the description of the presently preferred embodiments, in conjunction with the drawings, which now follow.

BRIEF DESCRIPTION OF THE DRAWINGS

The accompanying drawings illustrate presently preferred embodiments of the invention and, together with the description that follows, serve to explain the principles of the invention.

FIGS. 1, 2, 3, and 4 depict embodiments of the invention with a separate microbubble generating assembly and handheld device.

FIG. 5 may describe an embodiment of the invention using cross flow microbubble generation or an embodiment of the invention using rectified diffusion to stabilize shrinking, transient bubbles at a desired bubble size.

DETAILED DESCRIPTION OF PREFERRED EMBODIMENTS

Reference will now be made in detail to various suitable embodiments including a presently preferred embodiment of the invention as illustrated in the accompanying drawings. It will be understood that this description is exemplary and is to assist in understanding the invention and the principles of operation.

Figure 1:
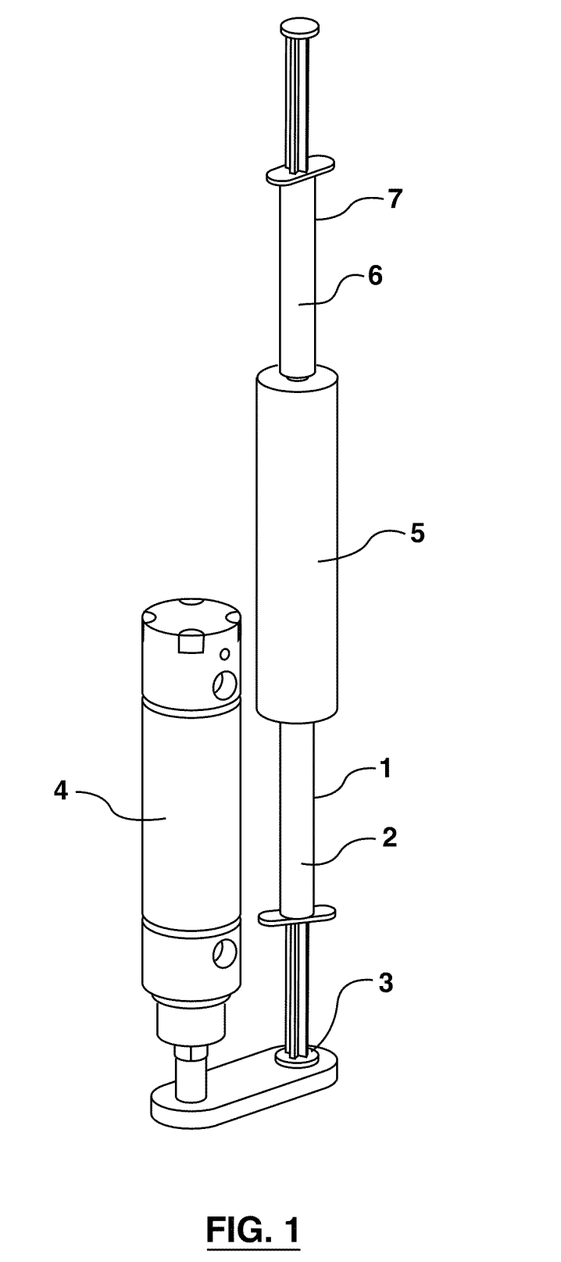
FIG. 1 depicts microbubble generation employing a pneumatic actuator.

FIG. 1 depicts a microbubble generating device that employs a pneumatic actuator to generate micro bubbles of varying sizes.

A generator syringe (1) is loaded with a surfactant saline solution (2). The generator syringe plunger (3) is withdrawn in order to infuse a quantity of air within the generator syringe (1) to achieve a desired liquid to air ratio.

The surfactant solution (2) may be comprised of a number of suitable, commercially available surfactants, for example detergents, lauric, oleic, palmitic or stearic acid, or micelle-based surfactants, in a sterile saline, a phosphate buffered saline, or other liquid suitable for injecting within the body. A plurality of surfactants, for example a Span 60 and Tween 80 combination, may be used. The surfactants may be melted, crushed, heated, stirred, mixed, or agitated within the liquid in order to ensure adequate solubility or distribution. The surfactant solution may require additional heating or agitation immediately prior to use. Agitation may be achieved by manual, mechanized, ultrasonic, or other suitable means. The solution may contain other additives to adjust viscosity, promote bioadhesion of the bubbles, or enhance effectiveness of a particular therapeutic agent.

A pneumatic actuator (4) and generator assembly (5) are connected to the generator syringe (1). The pneumatic actuator (4), driven by regulated, compressed gas (not shown), and controlled by a pneumatic control system (not shown), is used to drive the syringe plunger (3) in order to infuse the surfactant solution (2) and air mixture into the generator assembly (5) at a controlled flow rate.

Microbubbles are formed in the generator assembly (5) through an in-line flow focusing technique and a microbubble solution (6) is infused into a microbubble syringe (7) connected by an adaptor (not shown).

The microbubble syringe (7) is removed and the generator assembly (5) disconnected from the generator syringe (1). The generator syringe plunger (3) may be manually withdrawn in order to infuse an additional quantity of air within the generator syringe (1) to achieve a desired liquid to air ratio.

The generator assembly (5) is reconnected to the generator syringe (2) and the pneumatic actuator (4) is used to purge the generator assembly (5). A second microbubble syringe (not depicted) is connected to the generator assembly (5). The pneumatic actuator (4) is used to drive the surfactant solution (2) and air mixture through the generator assembly (5) at a controlled flow rate and to generate a second microbubble solution mixture (not shown) for infusion into a second microbubble syringe (not shown).

The second microbubbles generated may differ in size, concentration, and stability from the first bubbles generated, through the adjustment of procedural parameters, for example the liquid to air ratio, plunger flow rate, capillary tube and mix chamber geometry of the generator assembly, infusion of additional additives, or through the use of an alternative surfactant solution.

The microbubble generating assembly may employ a variety of means to drive the liquid and gas mixture, for example manual, hydraulic, mechanized, or a programmable electromechanical system such as a programmable syringe pump. The syringe pump could be any number of commercially available products, equivalent to a Braintree BS-8000 programmable syringe pump but suitable for human, veterinary, or research applications. The syringe pump drive force may be increased as required using mechanized means, for example through the addition of a drive spring or through pneumatic drive enhancement.

A liquid to air ratio in the order of 20:1 may be used to generate microbubbles from 1-5 micron in diameter, and a liquid to air ratio in the order of 5:1 to generate microbubbles in the 20 micron diameter range.

In an alternative embodiment of the invention, the surfactant solution (2) may be preloaded with a volume of air or other suitable gas. In this embodiment the liquid to air or liquid to gas ratio would be fixed, and the operator would not withdraw the plunger or infuse compressed gas into the surfactant solution (2) prior to delivering it through the generator assembly (5) in order to create microbubbles.

The microbubble generator assembly (5) may be oriented vertically in order to prevent air drawn into the surfactant solution (2) from migrating to the top of the generator syringe (1). This would ensure that an adequate mix of air and liquid is driven into the generator assembly (5) in order to create the desired microbubbles.

Figure 4:
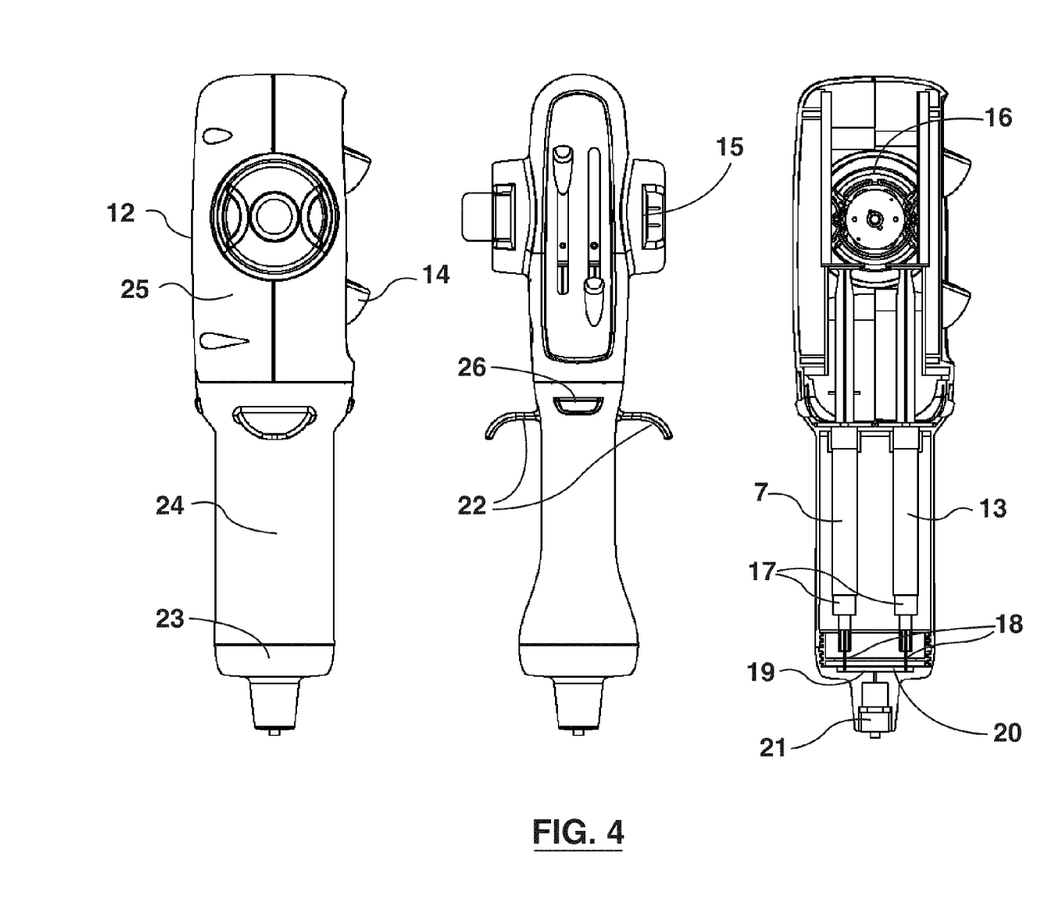
FIG. 4 depicts a handheld device used to selectively actuate four syringes in order to infuse two drugs or a drug and saline solution with varying concentrations and sizes of microbubbles for delivery within a patient.

The microbubble generator device depicted in FIG. 1 is used to infuse microbubble solutions into a syringe for loading into a hand held assembly as depicted in FIG. 4. In an alternate embodiment, the microbubble generator device (1) may be used as a stand-alone therapeutic or imaging device.

The microbubbles solution in a syringe (7) may be directly infused into a patient through catheter, needles or other means, acting as contrast media in order to enhance ultrasound imaging.

As a stand-alone therapeutic device, the surfactant solution (2) may contain a drug or other therapeutic agents. The surfactant solution (2) may also contain a volume of air or gas or the plunger may be withdrawn in order to add air or compressed gas may be infused in the surfactant solution (2). The gas or air loaded solution (2) would be driven through the microbubble generator assembly (5) and the subsequent drug and microbubble solution loaded into a syringe for infusion of the drug and microbubbles into the patient through a needle, catheter or other suitable means.

The means for verifying the generated bubbles size, homogeneity, and concentration in real time may be used with the microbubble generating device. For example, a commercially available product, a Coulter Multisizer, may be used to measure bubble characteristics through impedance measurements of bubble and carrier fluid samples.

Figure 2:
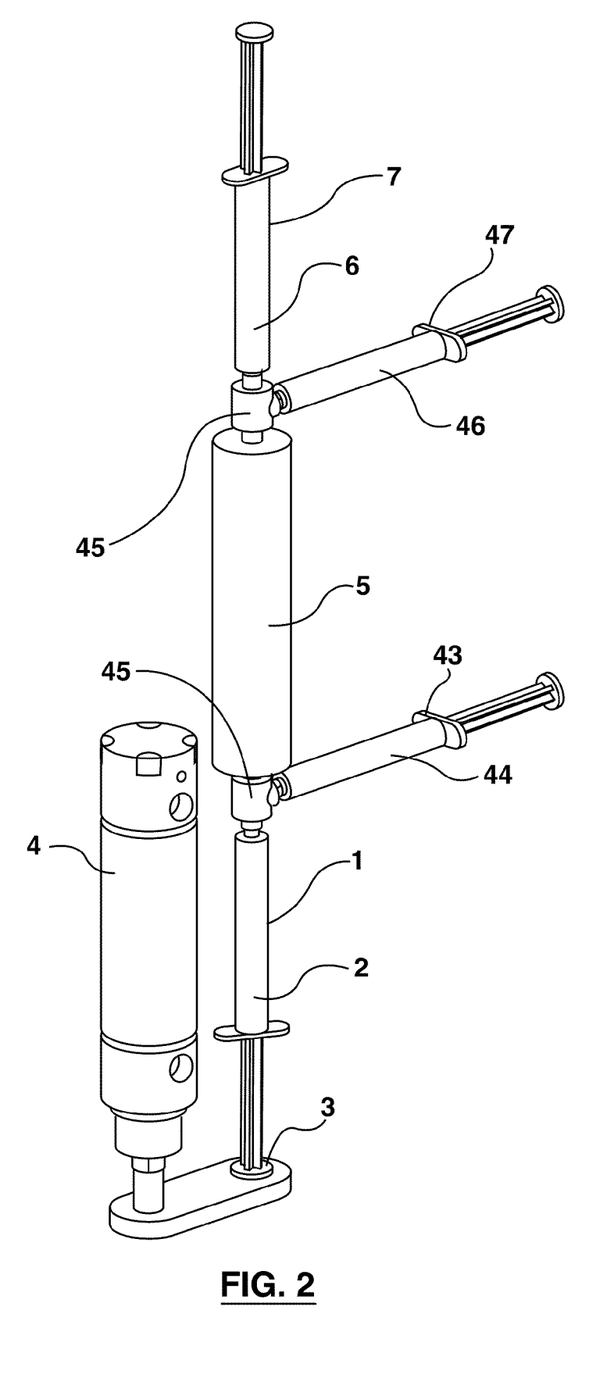
FIG. 2 depicts microbubble generation employing a pneumatic actuator with means to infuse additives on demand.

FIG. 2 depicts microbubble generation employing a pneumatic actuator with means for infusing additives on demand.

This embodiment is a variation of the microbubble generation system depicted in FIG. 1 with the additional means for infusing additives, either pre- or post-bubble generation, on demand.

The generator syringe (2) is connected to a three-way valve (45). The valve (45) would permit additive fluid (44) flow into the generator syringe (2) from a fluid supply such as a syringe (43) or a compressed gas canister (not shown) or other suitable means.

The additive fluid (44), or fluids, may be a variety of substances to improve treatment. For example, additional therapeutic agents may enhance treatment efficacy, additional surfactants may enhance bubble generation, and thickening agents may improve bubble generation and/or retention of a therapeutic agent in the diseased tissue.

The additive fluid (44) may be the gas used to form gas microbubbles. Gas additives may be compressed or pumped or driven by propellant, and may be air, $CO_2$, noble gases, oxygen, nitrogen, perfluorocarbon, or other types of suitable gases. It may be medical grade to lessen adverse effects on the patient. The operator may selectively adjust the valve (45) to infuse gas within the generator syringe (2) and then to deliver the gas and surfactant solution (2) through the generator assembly (5) in order to generate microbubbles. The compressed bubble gas may also be used to drive the pneumatic actuator (4).

Fluid additives (46) may be supplied on demand, post microbubble generation. A valve (45) would permit additive fluid (46) flow into the microbubble syringe (7) from a fluid supply such as a syringe (47) or a compressed gas canister (not shown) or other suitable means.

Figure 3:
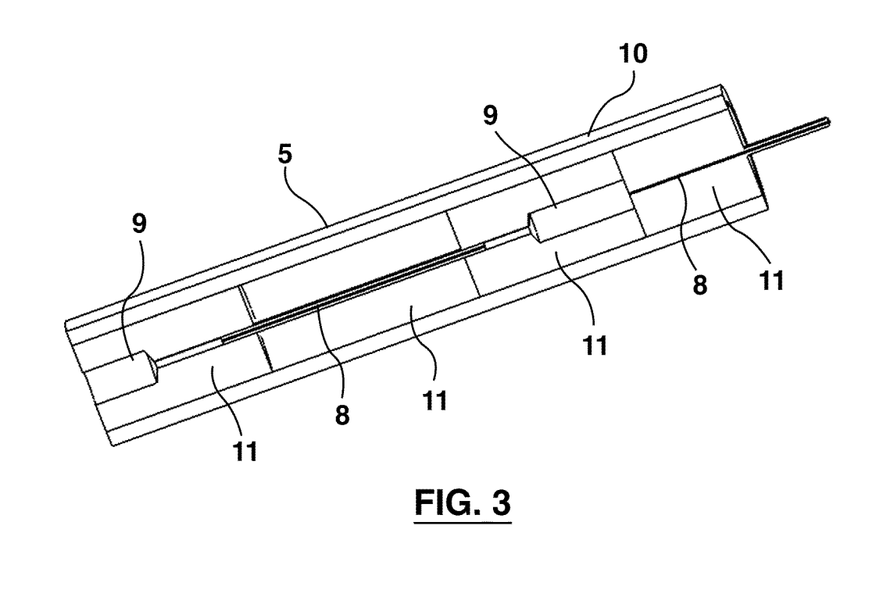
FIG. 3 depicts an in-line, flow focusing, microbubble generator assembly.

FIG. 3 depicts a cross-sectional view of the generator assembly.

The generator assembly (5) is comprised of a series of capillary tubes (8), mix chambers (9), and adaptors (not shown), which may be contained within an outer casing (10).

The number of capillary tubes and mix chambers arranged in series may range from one of each to eight of each or more. The inner diameter of the capillary tubes may be in the order of 50 to 1000 microns with 300 microns typical. The length of capillary tubing may vary, for example with a first tube 0.5 to 15 cm in length and subsequent tubes 1 to 10 cm in length. The mix chamber geometry may vary, with an inner diameter of 0.2 centimeters up to 2 centimeters, with 0.5 centimeters typical, and a length of 0.05 centimeters up to 5 centimeters, with 1 centimeter typical. The capillary tubes may be arranged in a straight line or may be offset to promote the mixing of bubbles and liquid in the mix chambers.

The capillary tubes and mix chambers may be fabricated in a variety of methods using a variety of materials. Material selection would permit sterilization of interior surfaces contacting the surfactant solution that is to be infused within a patient.

Stainless steel medical needles cut to length may be used to form the capillary tubes. The mix chambers may be machined from sections of plastic tubing (11), from plastic or metal material such as acrylic, Teflon, or brass, with a through hole drilled within which to fit the capillary tubes. Epoxy may be used to leak proof the mated tubing sections. Syringe adaptors may be standard leak tight adaptors such as Luer-lok. The entire assembly may be cast or molded or subsections fabricated and contained within a suitable casing (10) of steel, plastic, or other material.

Tube sections (11) may feature O-ring grooves within which to fit O-rings made of a suitable material such as silicon. The leak proof gap between tubing sections contained by the O-rings may form the mix chambers (9).

The cross sectional geometry of the capillary tubes (8), mix chambers (9), tube sections (11), and casing (10) may be circular, oval, elliptical, rectangular, or any suitable polygonal shape.

Generator assembly (5) sections may be comprised of commercial leak proof adaptors threaded or otherwise connected to each other. Alternate sections may be comprised of capillary tubes epoxied in place and adaptors forming the mix chambers. The advantage of this embodiment would be to combine the outer casing, mix chambers, and capillary tube housing in single, commercially available components.

The means for infusing additional additives to the surfactant solution on demand may also be incorporated within the generator assembly. Through holes with valves, plugs, or other suitable means may be incorporated into the generator assembly (5).

FIG. 4 depicts a front, side, and cross-sectional view of a handheld device that is separate from a microbubble generating device.

A handheld device (12) is loaded with four syringes. The syringes contain small air microbubbles, for example 5 micron diameter, in a saline solution (7), larger air microbubbles, for example 20 micron diameter, in saline (not shown), a drug (13), and a sterile saline solution (not shown).

Two actuators (14) on the handheld device (12) are used by the operator to select and manually drive either the drug (13) or the sterile saline solution (not shown). A control bevel (15) is used to select either the small microbubble syringe (7) or large microbubble syringe to be simultaneously actuated. The control bevel (15) is also used to adjust the concentration of microbubbles in the drug by engaging a gearbox assembly (16).

The gearbox assembly (16) is comprised of racks and pinions (not shown). The control bevel (15) is used to selectively engage different pinions to the drive racks linked to the manual actuators (14) and various gear ratios can be selected to vary the ratio of the drug syringe plunger travel to the microbubble syringe plunger travel and hence to adjust the concentration of microbubbles within the drug in real time.

The drug (13) and microbubbles in saline (7) are driven through needle adaptors (17), short needles (18), and into a shallow, sterile chamber (19) sealed by a septum (20). The drug and microbubble mixture is driven through the patient needle adaptor (21) and through a patient needle (not shown) to be infused within a patient.

During the handheld device (12) loading, the four syringe needles (18) puncture the septum (20). Alternatively, the four syringes could be attached to sterile fluid conduits, with, for example, a single four-way, or two-two way connectors, providing a fluid path to the patient needle. The advantage of a septum chamber is to permit a faster syringe loading, which may be important if the microbubbles' persistence is in the order of minutes or less. The septum chamber may also reduce the risk of compromising the sterility of the injectate by permitting a simpler loading procedure.

To aid drug delivery ergonomics, the physician may engage two finger grips (22) to permit single hand use, thus enabling the physician to hold an ultrasound transducer with the other hand.

The handheld device (12) is assembled through threading the septum casing (23) into the syringe casing (24), and connecting the syringe casing (24) to the gearbox casing (25) with snap fits (26). Alternatively, the septum and syringe casings could be a single, sterile consumable, with the septum ultrasonically welded into a molded housing.

A variety of casing configurations, fluid connection means, and assembly procedures may be used. The fluid vessels could be connected to a common patient needle or catheter adaptor through two, three, or four way fluid conduits, valves, or other suitable means including mechanical or electronically controlled valve systems.

The handheld device (12) could be used to deliver a plurality of therapeutic agents and other injectates at varying concentrations and combinations. For example, drugs could be combined with ultrasound contrast agents, drugs combined with alternate acoustically activated drug delivery systems, such as polymeric micelles or microsponges loaded with chemotherapy, and the like.

The term "drug" as used in the specification can be liquid, a solution, a suspension, solid particulates in a solution, etc. The liquid drug may be any suitable therapeutic agent or agents that can be delivered under pressure through a needle or catheter, such as a single organic or inorganic drug, a solution of different drugs, drug particles or radiolabelled particles suspended in a fluid, a time release delivery system such as drug eluting microspheres or other embedded drug systems suspended in a fluid, an acoustically activated drug delivery system, a targeted drug delivery system or agent, a bioadhesion additive, an embolization gel, or other therapeutic agents.

Figure 5:
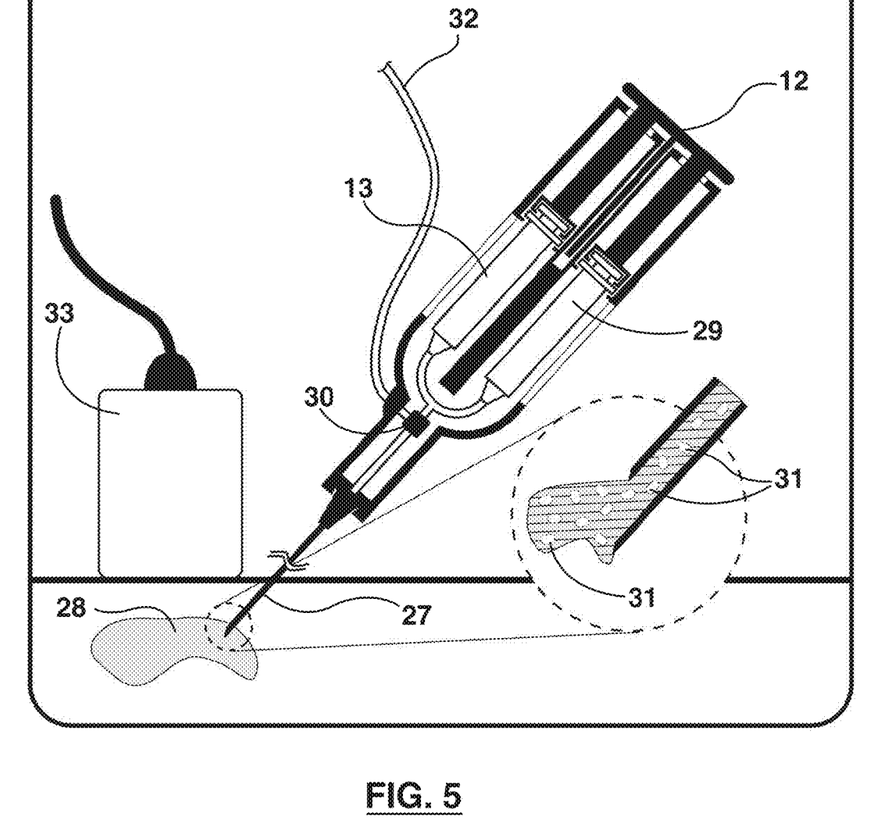
FIG. 5 depicts embodiments of the invention where microbubble generation occurs within a handheld device for direct delivery into a patient and acoustic activation.

FIG. 5 depicts a cross sectional and detailed view of an embodiment of the invention where microbubble generation occurs within a handheld device for direct delivery into a tumour and acoustic activation.

A physician uses the handheld device (12) to position a patient needle (27) at the desired point of interest, for example a tumour (28). The handheld device is loaded with two syringes containing a drug (13) and a sterile saline solution (29). A Y-shaped conduit connects the outlet of each of the syringes and merges the two fluid paths into a single fluid path connected to a hollow patient needle (27) that may be inserted into the point of interest (28), defining a path of fluid flow into the patient's body.

A microbubble generating system (30) is connected to the fluid flow path in order to infuse gas microbubbles (31) within the drug (13) or saline (29). Compressed gas contained within a cylinder (not shown), and controlled by a regulator (not shown), is driven through a fluid conduit (32) into the generating system (30) and transformed into bubble form through cross flow or other means.

After infusion of the drug (13) and microbubbles (31) within the tumour (28), an ultrasound transducer (33) is used to apply ultrasound energy. The resulting acoustic activation may resonate or destroy the microbubbles (31).

Acoustically activating a micro or nano bubble, either a bubble comprised of a drug or a non-therapeutic bubble within a drug carrier, with ultrasound may be used:

- to activate the pharmacological activity of a therapeutic agent, such as enhancing drug transport through tissues and across cell membranes, and, or
- to create a local hyperthermic condition that can enhance the destruction of diseased tissue such as cancerous tissue, and, or
- to further enhance the drug uptake of acoustically activated drug delivery systems by means such as increasing the local cavitations and microstreaming The handheld device (12) may be used to perform precision drug delivery to a point of interest. Once the needle (27) is positioned at a tumour (28), a physician may pulse the saline solution (29) infused with gas microbubbles (31) at different flow rates, flow volumes, and needle positions, and monitor the liquid's perfusion in the patient using the ultrasound display (not shown). Once satisfied, the physician may then infuse the drug (13) with microbubbles (31), and verify the drug delivery precision real time. Precision drug delivery avoids debilitating side effects to healthy tissue and ensures that the entire tumour volume is treated and may be destroyed.

The handheld device (12) may be used to enhance the needle visibility during ultrasound-image guidance. If the needle (27) fades from the ultrasound display at a depth within a patient, the physician may pulse a small quantity of saline solution (29) infused with gas microbubbles (31) a brief distance in order to clearly indicate the position of the needle tip and enable the safe guidance of the needle (27) to the tumour (28).

As depicted, the syringes, conduits and fluid housing are contained in a hand held frame that includes a mount for attachment of the needle. The frame may be variously shaped containing or supporting one or more of fluid containers, conduits, and injection means. The bubble generating means may also be supported in the frame. The frame may also support various other controls, regulators, valves, heat sources refrigeration sources, temperature sensors, pressure sensors, flow sensors, fluid switch mechanisms, flow rate regulators, ultrasound transducers, transducer array, insulation, and the like. The frame may be provided with a handle. The frame may also support meters, controllers, controller I/O, display and power source. Alternatively, one or more of these components may be separate from the frame but systemically electrically linked to other components on the frame.

The handheld assembly (12) may alternatively be provided with a single syringe or a plurality of syringes, or other vessels containing fluids for delivery to a patient. The fluid from other vessels may be delivered under pressure using manual or mechanical means and may be connected to the single conduit. The drug (13) may be delivered to the point of interest by manual means, for example by depressing a syringe plunger, mechanized, pneumatic, hydraulic, or electro-mechanical means.

The microbubble generating system (30) may be comprised of a cross flow microbubble generation system or an alternate system. The microbubble generating system (30) may include a transducer or transducer array in order to permit the stabilization of shrinking bubbles at a particular desired bubble size through rectified diffusion.

In an embodiment of the invention employing rectified diffusion, a transducer or transducer array affixed to the device is used to apply ultrasound energy to shrinking microbubbles contained within a stabilization chamber. This embodiment may include controls to vary the frequency, intensity, and mode of the ultrasound. Varying the ultrasound frequency permits real time adjustment of the bubble size, for example the operator may choose to stabilize the shrinking bubbles at 10 microns or 5 microns. The associated power source and controls for the transducer or transducer array may be incorporated within the handheld device, tethered to it, or linked via wireless means.

Non-homogenous bubbles may be generated using the device (12), and these may shrink to a desired size, and be stabilized at that size, within seconds or minutes. The microbubbles may then be infused within the patient using a needle, catheter, or other means, prior to their being acoustically activated using the ultrasound transducer (33) in contact with the patient's body. During infusion, the bubbles will not be subjected to a stabilizing ultrasound energy and will shrink. Therefore if the operator desires 5 micron bubbles within the patient at the point of interest (28), they may select to stabilize the bubbles at 7 to 10 microns within the device (30) and these bubbles may shrink during infusion, or within the patient, to the desired size.

A utility of combination therapy, the means for delivering a variety of therapeutic agents at a point of interest, is to enhance treatment efficacy for indications such as drug resistant cancer tumours. Further utility is obtained by the flexibility of varying treatment to meet a patient's specific needs.

A number of relatively biologically harmless fluids could serve as the bubble carrier fluid, such as sterile saline solution, phosphate buffered saline, sterile water, blood, or other fluids. The carrier fluid may include additives to alter its viscosity in order to promote the creation and stability of transient bubbles. The carrier fluid may include additives to promote the efficacy of the therapeutic agent, such as a drug to prevent infection or to aid or to combat the migration of the drug.

The pressure may be supplied to the drug using a variety of means including a manual syringe or an electromechanical fluid pump. The pressure required is dependent on a variety of factors, such as the size and homogenity of the bubbles desired, viscosity of the drug, and the like.

Figure 6:
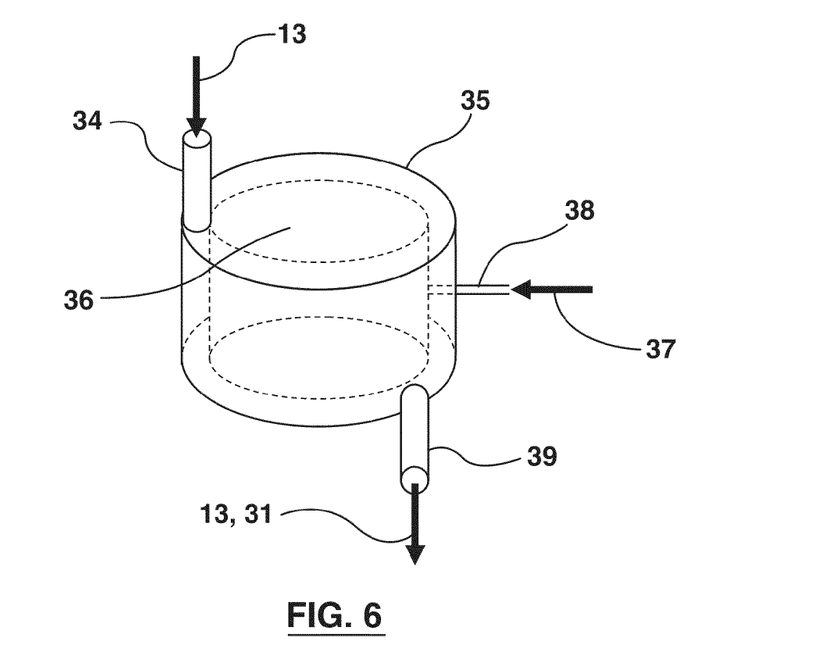
FIGS. 6 and 7 depict detailed views of cross flow microbubble generation.
Figure 7:
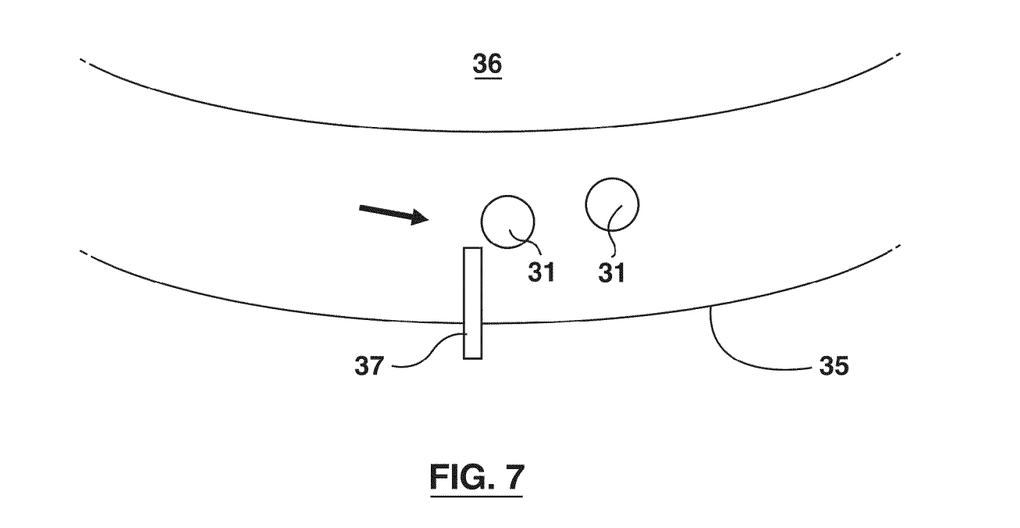

FIGS. 6 and 7 depict an orthogonal and plan view of details of an embodiment of the invention employing cross flow microbubble generation.

A liquid drug (13) is driven through a fluid conduit (34) into a cross flow chamber (35). A rotating drum (36) induces recirculating drug flow in the chamber (35). Compressed gas (37) is driven through a pipette (38) into the cross flow chamber (35) and is transformed into microbubbles (31). The cross flow motion of the liquid drug (13) may promote bubble detachment and result in smaller, more homogenous bubble formation than would be possible with a static system.

The pipette may have a single opening, ranging in diameter from one half to five microns in diameter or greater. The pipette may have a plurality of openings, for example a filter membrane with hundreds of nano or micron sized openings may be used.

The drug (13) infused with gas microbubbles (31) is driven through an exit fluid conduit (39) for infusion into a patient.

The rotating drum may be actuated by a number of means, for example through a drive shaft connected to a mechanized or electro-mechanical motor positioned outside the cross flow chamber, or using commercially available magnetic stirrer technology whereby a rotating drive shaft would not be required.

Figure 8:
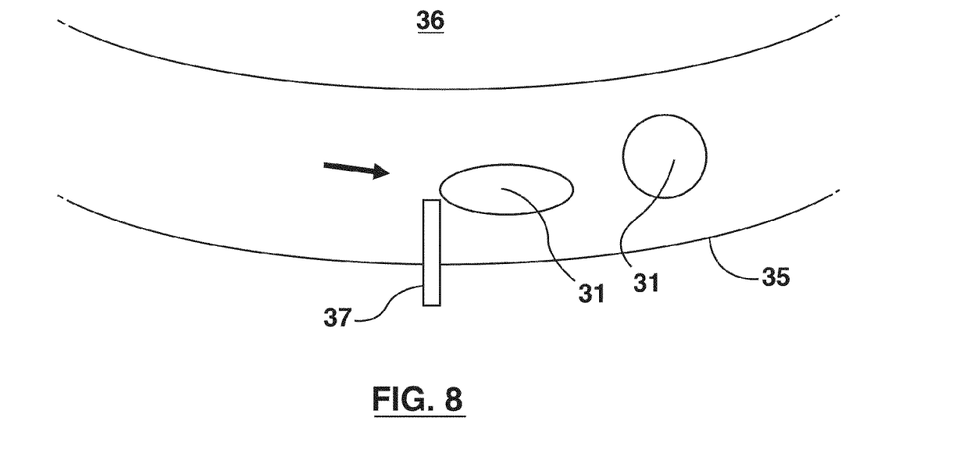
FIGS. 8, 9, 10, and 11 depict detailed views of enhanced bubble detachment means for cross flow microbubble generation.

A potential drawback of the cross flow system is that the microbubbles (31) may have a tendency to grow in the direction of the cross flow prior to detachment, as depicted in FIG. 8, and hence have a bubble diameter twenty to fifty times the diameter of the pipette opening. Small, 1 to 5 micron bubbles are typically used for acoustic activation applications and it is desirable to maximize the pipette diameter for ease of fabrication. Therefore it is advantageous to promote microbubble detachment such that the microbubble diameter is in the order of two to ten times the pipette diameter.

Figure 9:
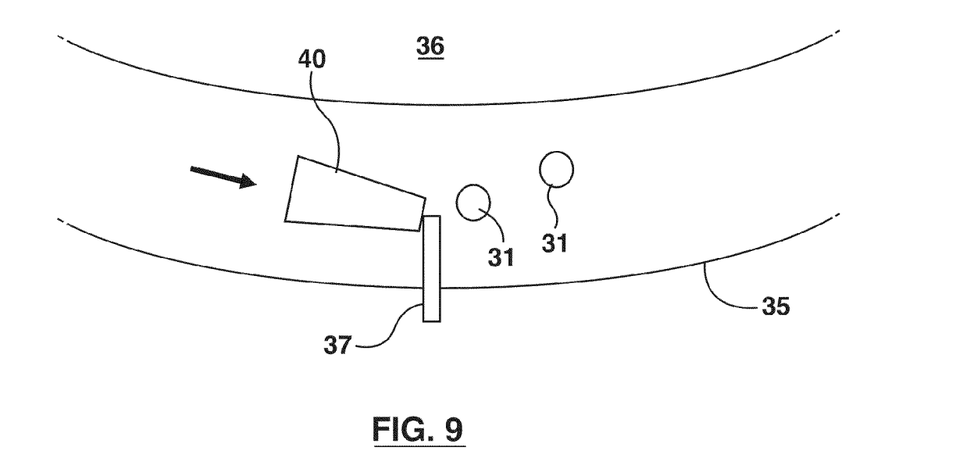

FIG. 9 depicts a funnel (40) used to focus the cross flow on the forming microbubble neck and hence promote detachment of the bubbles (31) at a relatively small size.

Figure 10:
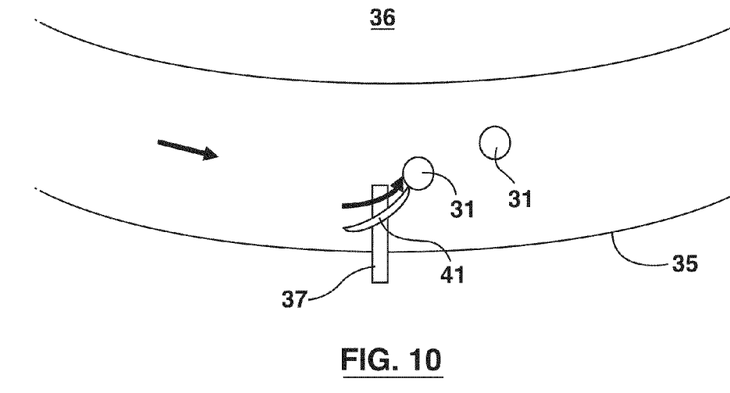

FIG. 10 depicts a curved channel, or hydrofoil, (41) used to direct the cross flow to the distal side of the pipette (37), to prevent bubble propagation in the direction of the cross flow, and hence to promote detachment of the bubbles (31) at a relatively small size.

Figure 11:
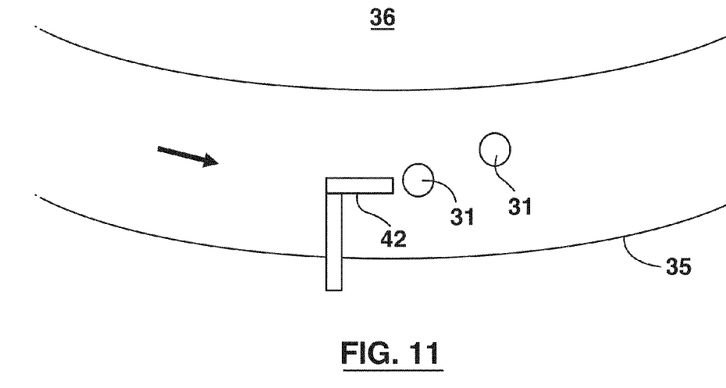

FIG. 11 depicts right-angled pipette, (42) used to deliver the gas flow in the direction of the liquid cross flow to prevent bubble propagation in the direction of the cross flow, and hence to promote detachment of the bubbles (31) at a relatively small size.

Other means for preventing microbubbles from propagating in the direction of the cross flow and to promote bubble detachment include the means to rotate or spin the pipette along its axis to create additional shear force and prevent the forming bubble from sheltering behind the pipette stem. An electromechanical or transducer vibration source could also be used to periodically impact the pipette in order to promote bubble detachment.

The various embodiments of the device may be comprised of or used with standard, commercial, medical components such as needles, needle adaptors, catheters, syringes, guide wires, infusion pumps, fluid conduits, leak proof fittings, meters, laparoscopes, endoscopes, probes, multiple lumen delivery means and the like. The various embodiments of the device may be comprised of specialized components with attributes such as MRI compatible materials, coatings to enhance the image guidance of the device, and the like. Fluid vessels, such as syringes, may be attached to the handheld assembly using means such as adjustable clamps or connected to the handheld assembly using means such as fluid conduits.

A medical device such as disclosed in PCT/CA2004/000174 which is incorporated herein by reference may be provided with an additional means for generating micro or nano scale bubbles. For example, micro or nano scale bubbles may be used to enhance the ultrasonic visibility of a needle as disclosed in PCT/CA2004/000174 and may also be used to permit therapy enhanced by acoustic activation as disclosed in this application.

A medical device such as disclosed in U.S. No. 60/567,453 which is incorporated herein by reference, may be provided with an additional means for generating micro or nano scale bubbles. For example, means to generate transient micro or nano scale bubbles to permit therapy enhanced by acoustic activation as disclosed in U.S. No. 60/567,453 may also be used in combination with means to generate bubbles, such as rectified diffusion and cross flow, as disclosed in this application.

CONCLUSION

Devices for generating bubbles for infusion within a patient and for activation by an ultrasound source are disclosed. The devices may enhance the efficacy of a treatment by increasing cellular uptake of a drug at the point of interest and may reduce undesired side effects.

The device may be comprised of a handheld assembly or system comprising injection means for injecting fluids into a patient such as a needle or catheter, fluid containers, fluid discharge means, and a bubble generating means to generate micro or nano scale bubbles.

The device may include means for controlling or regulating the fluid supply, such as flow controls, pressure sensors, flow sensors, fluid switch mechanisms, regulators or valves. The device may include meters, controllers, controller I/O, display, and power source.

These claims, and the language used therein, are to be understood in terms of the variants of the invention, which have been described. They are not to be restricted to such variants, but are to be read as covering the full scope of the invention as is implicit within the invention and the disclosure that has been provided herein.

The foregoing has constituted a description of specific embodiments showing how the invention may be applied and put into use. These embodiments are only exemplary. The invention in broader, and more specific aspects, is further described and defined in the claims that now follow.

What is claimed is:

1. A device for generating bubbles for introduction into a body comprising: a generator syringe having a plunger slidably disposed within the generator syringe and a first connector part distal from the plunger, the generator syringe preloaded with a preload of a liquid carrier component and a gas component in a predetermined liquid to gas ratio determined to provide bubbles of preselected size; a generator assembly having a second connector part at an inlet, the second connector part being complementary to the first connector part so that the generator assembly connects to the generator syringe at the inlet to form a unitary body; the generator assembly including an in-line flow focusing system having longitudinally spaced and interconnected first capillary tube and second mix chamber respectively of comparatively smaller and comparatively larger cross-sections cooperative to provide bubbles as a result of travel of said preload of a liquid carrier component and a gas component in a predetermined liquid and gas ratio through said longitudinally spaced and interconnected first capillary tube and second mix chamber respectively of comparatively smaller and comparatively larger cross-sections of said in-line flow focusing system; and an actuator driving the plunger for applying a pressure to the generator syringe causing the preload of liquid carrier component and gas component in said predetermined liquid to gas ratio to travel from the generator syringe through the comparatively smaller and comparatively larger capillary tube and mix chamber of said in-line flow focusing system of the generator assembly to an outlet of the generator assembly resulting in said bubbles of said preselected size.

2. A device according to claim 1 further comprising: a second syringe for supplying a second fluid to the generator assembly.

3. The device according to claim 2, wherein the second fluid is an additional therapeutic agent.

4. The device according to claim 3, further comprising an injection means communicating with the outlet.

5. The device according to claim 1, wherein the carrier component further comprises one member selected from the group consisting of a therapeutic agent, a carrier, an additive, a stabilizer, a bioadhesive, and a combination thereof.

6. The device according to claim 5, wherein the therapeutic agent includes one or more of: a liquid drug, organic or inorganic; a solid drug suspended in a fluid; an acoustically activated drug delivery system, suspended in a fluid; a therapeutic chemical including ethanol or acid; an embolization fluid, gel, or gel suspension; a photodynamic drug; a radioisotope labelled drug or particle; and an imaging system contrast agent for imaging systems including CT scans, MRI, ultrasound, or X-ray.

7. The device according to claim 1, wherein the device is a handheld device.

8. The device according to claim 1, further comprising means for stabilizing transient bubbles at a desired bubble size comprising: means for directing the bubbles to a stabilizing chamber; and means for transmitting an ultrasonic pulse at the bubbles for a sufficient time period for the bubbles to shrink to and stabilize at a size corresponding to the resonant frequency, or a harmonic, of the ultrasonic pulse.

9. The device according to claim 1, further comprising temperature control means for modulating a temperature of the preload.

10. The device of according to claim 1, further comprising a storage vessel positioned downstream of the generator assembly for receiving the bubbles.

11. A system for acoustically activating bubbles comprising: a device according to claim 1; and acoustic activation means for generating acoustic pulses; wherein the acoustic activation means is selected from the group consisting of an ultrasound transducer, and a transducer array for transmitting pulses; and wherein acoustic activation of the bubbles induces a member selected from the group consisting of inertial cavitations, non-inertial cavitations, bubble resonance, and bubble destruction and a combination thereof.

12. A system for enhancing high intensity focussed ultrasound (HIFU) treatment comprising: a device according to claim 1; and HIFU means for generating high intensity focused ultrasound pulses; wherein the HIFU means is selected from the group consisting of a HIFU probe for minimally invasive tumour ablation, an extracorporeal, high intensity ultrasound transducer, and a transducer array for transmitting pulses; wherein the high intensity focused ultrasound means comprises means for focusing the pulses; and wherein the HIFU energy applied to the bubbles induces a member selected from the group consisting of inertial cavitations, non-inertial cavitations, bubble resonance, bubble destruction, and a combination thereof.

13. A method for acoustically activating bubbles comprising: using a device according to claim 1 to generate bubbles; introducing the bubbles to a point of interest in a body; and applying acoustic pulses at the bubbles; wherein the acoustic pulses are generated by acoustic activation means, selected from the group consisting of an ultrasound transducer, and a transducer array for transmitting pulses; and wherein the acoustic activation of the bubbles induces a member selected from the group consisting of inertial cavitations, non-inertial cavitations, bubble resonance, bubble destruction, and a combination thereof.

14. A method for enhancing high intensity focussed ultrasound (HIFU) treatment comprising: using a device according to claim 1 to generate bubbles; introducing the bubbles to a point of interest in a body; and applying HIFU pulses at the bubbles; wherein the HIFU means is selected from the group consisting of a HIFU probe for minimally invasive tumour ablation, an extracorporeal, high intensity ultrasound transducer, and a transducer array for transmitting pulses; wherein the HIFU means comprises means for focusing the pulses, and wherein the HIFU energy applied to the bubbles induces a member selected from the group consisting of inertial cavitations, non-inertial cavitations, bubble resonance, bubble destruction, and a combination thereof.

15. A method of treatment of cancers and tumours, including retinoblastoma, esophageal and liver cancers, vascular disease, or neurological disease comprising: using a device according to claim 1 to generate bubbles; introducing the bubbles to a point of interest in a body; generating acoustic pulses; and applying the acoustic pulses at the bubbles; wherein the acoustic activation means is selected from the group consisting of an ultrasound transducer; and a transducer array for transmitting pulses; and wherein the acoustic activation of the bubbles induces a member selected from the group consisting of inertial cavitations, non-inertial cavitations, bubble resonance, bubble destruction, and a combination thereof.

16. A method for inducing cell necrosis in diseased tissue comprising: using a device according to claim 1 to generate bubbles; introducing the bubbles to a point of interest in a body; and applying high intensity focused ultrasound (HIFU) pulses at the bubbles; wherein the high intensity focussed ultrasound is applied using means selected from the group consisting of a HIFU probe for minimally invasive tumour ablation, an extracorporeal, high intensity ultrasound transducer, and a transducer array for transmitting pulses; wherein the pulses are focused using a time reversal acoustics array, and wherein the HIFU pulses applied to the bubbles induces a member selected from the group consisting of inertial cavitations, non-inertial cavitations, bubble resonance, bubble destruction, and a combination thereof.

\* \* \* \* \*